(12) United States Patent
Bond et al.

(10) Patent No.: US 9,285,351 B2
(45) Date of Patent: Mar. 15, 2016

(54) SENSOR ASSEMBLY FOR HYGENIC MATERIAL PROCESSING SYSTEMS

(75) Inventors: Richard J. Bond, Pattersonville, NY (US); Vikram Bose-Mullick, Fonda, NY (US); Apurva Naik, Niskayuna, NY (US); Joseph Mecca, Gloversville, NY (US)

(73) Assignee: ANDERSON INSTRUMENT Co., INC., Fultonville, NY (US)

( * ) Notice: Subject to any disclaimer, the term of this patent is extended or adjusted under 35 U.S.C. 154(b) by 153 days.

(21) Appl. No.: 13/983,433

(22) PCT Filed: Feb. 3, 2012

(86) PCT No.: PCT/US2012/000057
§ 371 (c)(1),
(2), (4) Date: Nov. 8, 2013

(87) PCT Pub. No.: WO2012/106053
PCT Pub. Date: Aug. 9, 2012

(65) Prior Publication Data
US 2014/0350862 A1    Nov. 27, 2014

Related U.S. Application Data

(63) Continuation of application No. 13/020,586, filed on Feb. 3, 2011, now abandoned.

(51) Int. Cl.
*G01L 27/00*    (2006.01)
*G01N 33/02*    (2006.01)
*G01D 11/26*    (2006.01)
(Continued)

(52) U.S. Cl.
CPC ............... *G01N 33/02* (2013.01); *G01D 11/26* (2013.01); *G01F 15/14* (2013.01); *G01F 23/00* (2013.01); *G01F 25/0007* (2013.01); *G01F 25/0061* (2013.01); *G01K 1/14* (2013.01); *G01N 33/15* (2013.01)

(58) Field of Classification Search
None
See application file for complete search history.

(56) References Cited

U.S. PATENT DOCUMENTS 8,801,273 B2 *   8/2014   Parasnis et al. ................. 374/45
2014/0182350 A1 *  7/2014   Bhavaraju et al. ............. 73/1.02

FOREIGN PATENT DOCUMENTS

WO    WO 2007/039931    *   4/2007
WO    WO 2007087705     *   8/2007

*Primary Examiner* — Robert R Raevis
(74) *Attorney, Agent, or Firm* — Romi Bose

(57) ABSTRACT

A sensor assembly includes a replaceable sensor module and an assembly housing. The assembly housing contains an assembly housing processor and an electrical connector connected to the processor. The replaceable sensor module has an enclosure adapted to be mounted in a position to sense a process variable, a process variable transducer positioned in said enclosure so as to be exposed to the process variable, and a non-volatile memory having stored therein specific profiling data for the sensor module. The assembly housing processor has data representing a desired sensor assembly output characteristic, and is responsive to receipt of specific profiling data and to the data representing the desired sensor assembly output characteristic to calibrate the sensor assembly to provide the desired sensor assembly output characteristic when connected to the sensor module having the specified profiling data. Radial and axial seals are provided for the openings in the assembly housing. Measurement of loop current ($I_L$) in a two-wire loop current communication system for the sensor assembly and detection of sensor aging are also included.

14 Claims, 10 Drawing Sheets

(51) Int. Cl.
*G01F 25/00* (2006.01)
*G01F 15/14* (2006.01)
*G01F 23/00* (2006.01)
*G01K 1/14* (2006.01)
*G01N 33/15* (2006.01)

SENSOR ASSEMBLY FOR HYGENIC MATERIAL PROCESSING SYSTEMS

CROSS REFERENCE TO RELATED APPLICATIONS

This application is a continuation of U.S. Nonprovisional patent application Ser. No. 13/020,586 filed Feb. 3, 2011 and a national stage application related to PCT Application number PCT/US2012/000057 filed Feb. 3, 2012. Those applications are incorporated by reference herein in their entirety for all purposes and this application claims the benefit of those applications for all applicable purposes.

STATEMENT REGARDING FEDERALLY SPONSORED RESEARCH

Not Applicable.

FIELD OF THE INVENTION

This disclosure relates to sensor assemblies for use in automated process control systems, and particularly to such sensor assemblies with improved reliability and functionality for use in hygienic material processing systems.

BACKGROUND OF THE INVENTION

This section provides general background information related to the present disclosure and the background information is not necessarily prior art.

Automated process control systems are conventionally used in various industries, such as biotechnology, beverage, dairy, food, and pharmaceutical manufacturing. These systems rely upon the measurement of process parameters (pressure, temperature, flow rate, fluid level, etc.) which are sensed by sensor assemblies. These sensor assemblies not only sense the particular process parameter desired at that particular point in the process, but also transmit the sensed values of the parameter to the automated process control system for appropriate action by the control system. That is, the sensor assemblies typically have both a sensing function and a communications function. Prior art sensor assemblies are conventionally single integrated units (i.e., includes the sensor function and the communications/signal processing in a single physical housing). With conventional prior art sensor assemblies, the entire assembly must be replaced when the sensing portion fails.

The housing for conventional sensor assemblies vary widely depending upon various factors, including (1) type of process connection, (2) parameter range for operation, (3) signal output (e.g., 4-20 ma, digital or field bus), and (4) orientation of installation. Although it is possible to keep a complete inventory of the sensor assemblies needed to keep the process line functioning, that can be an expensive proposition which some industries typically forgo. For example, the dairy facilities frequently do not stock a complete inventory of sensor assemblies. If the proper sensor assembly is not available, for whatever reason, when an installed assembly fails, production must be shut down until the proper sensor assembly is obtained and installed. This can be an expensive inconvenience for companies located near sources of replacement sensor assemblies. It can become an even more serious inconvenience when the plant is located in remote areas or in emerging countries with limited infrastructure.

One possible solution is to replace only the sensing portion of the assembly, since that is the portion that typically fails. That would drastically reduce the inventory that would be required to maintain full production. But this presents a problem: how to calibrate the sensor assembly in the field. As noted above, the sensor assembly includes both a sensing function and a communication function. Calibration of the sensor assembly involves ensuring not only that the sensing portion is supplying signals at the desired levels for the particular process parameter value being measured, but also that the communication part of the sensor assembly properly recognizes the output of the sensing portion and accurately communications the proper value of the proper parameter to the automated process control system. Such calibration in the field can be difficult. Since field calibration is not a common occurrence, it is prone to error if attempted by a local technician who typically lacks the needed expertise and can be a cause of further delay and expense if done by a specialist, who typically must travel to the processing facility to effect the replacement.

In many industries, e.g., dairy or brewing, sensor assemblies are subjected to high levels of humidity and moisture in general. This operating environment can also be true for tropical locales, even for typically "dry" material processing systems. The electronics in sensor assemblies can be extremely sensitive to unwanted moisture. Unwanted moisture can enter existing sensor assemblies (and potentially damage the electronics) not only in high humidity conditions, but also when the housing for the assembly is dented or otherwise damaged in such a way as to interfere with any moisture seals which are built into the sensor assembly. Existing sensor assemblies typically have visual displays incorporated into the assembly for displaying to a user the value of the particular parameter being measured. These displays are typically seen through a transparent cover. In high humidity conditions, this cover can accumulate moisture, thereby obscuring the view of the visual display in conventional sensor assemblies. The transparent enclosure, of course, must also be attached to the sensor assembly housing in such a way as to prevent the passage of moisture to the interior of the housing, but this goal is not always satisfactorily achieved with existing sensor assemblies. Frequently it is not possible for the person installing the transparent cover to determine whether the cover has been properly installed on the sensor assembly housing or to determine whether a moisture-tight seal has been achieved.

SUMMARY OF THE INVENTION

This section provides a general summary of the disclosure, and is not a comprehensive disclosure of its full scope or all of its features.

In accordance with the various embodiments of the present invention, this invention relates to an improved sensor assembly which provides for easy sensor replacement. The various embodiments can include a sensor assembly with an auto-calibrated output, a sensor assembly which simplifies inventory and supply chain problems, such a sensor assembly which is less complex to install, use and maintain, a sensor assembly which is particularly suited for hygienic processing environments such as food, dairy, brewery and pharmaceutical industry, and a sensor assembly which reduces the risk of moisture ingression due to physical damage to sensor assembly sealing surfaces. Yet other embodiments include a sensor assembly which minimizes the risk of moisture or other contamination accumulating on the transparent cover of the assembly, a sensor assembly which provides a positive indication such as a tactile or a visual indication when the seals between the transparent cover and the housing are properly seated, and a sensor assembly which provides redundant sealing against moisture ingression with two different failure modes. Other objects and features of yet alternative embodiments will be in part apparent and in part pointed out herein.

In the present embodiment of the invention, a sensor assembly for use in an automated process control system includes a replaceable sensor module, an assembly housing containing an assembly housing processor and an electrical connector connected to the processor and accessible by the automated process control system. The replaceable sensor module includes an enclosure adapted to be mounted in a position to sense a process variable, a process variable transducer positioned in the enclosure so as to be exposed to the process variable, and a non-volatile memory having stored therein specific profiling data for the sensor module. The assembly housing processor in the assembly housing has data representing a desired sensor assembly output characteristic, and is responsive to receipt of the specific profiling data and to the data representing the desired sensor assembly output characteristic to calibrate the sensor assembly to provide the desired sensor assembly output characteristic when connected to the sensor module having the specified profiling data.

In a second embodiment of the present invention, a sensor assembly includes a replaceable sensor module containing at least one transducer and at least one electronic circuit connected to the transducer, and an assembly housing containing at least an assembly housing processor and an electrical connector connected to the processor. The assembly housing has a cover secured thereto, and also has an opening for accepting a plug body through which passes at least one electrical connector. The assembly housing has at least two paths for migration of moisture from the exterior of the assembly housing to the interior of the assembly housing. At least one axial seal is positioned along a first of the moisture migration paths to resist the passage of moisture from the exterior of the assembly housing to the interior of the assembly housing. At least one radial seal is also positioned along the first moisture migration path to resist the passage of moisture from the exterior of the assembly housing to the interior of the assembly housing.

A third alternative embodiment of the present invention includes a method of operating a sensor assembly in a hygienic material processing system includes sensing a process variable using at least one transducer and at least one electronic circuit connected to the transducer, periodically automatically testing an electrical characteristic of the transducer, the testing occurring at a time other than when the process variable is being sensed, providing at least one threshold for the value of said electrical characteristic, and indicating when the electrical characteristic has gone over the threshold.

In yet a fourth embodiment of the present invention, a sensor assembly for use in an automated process control for a hygienic material processing system includes a two-wire current loop communications link communicating sensor data to the automated process control. The current in the loop corresponds to the measured value of the process variable. Feedback from the current loop is used to control the magnitude of the current and to generate a display of the loop current for the user.

Further areas of applicability will become apparent from the description provided herein. The description and specific examples in this summary are intended for purposes of illustration only and are not intended to limit the scope or the claims of the present disclosure.

In the following detailed descriptions, certain other exemplary embodiments of the present invention are described.

DESCRIPTION OF THE DRAWINGS

In the accompanying drawings which form part of this specification.

Similar reference characters indicate similar parts throughout the several views of the drawings.

Corresponding reference numerals indicate corresponding steps or parts throughout the several figures of the drawings.

Figure 1:
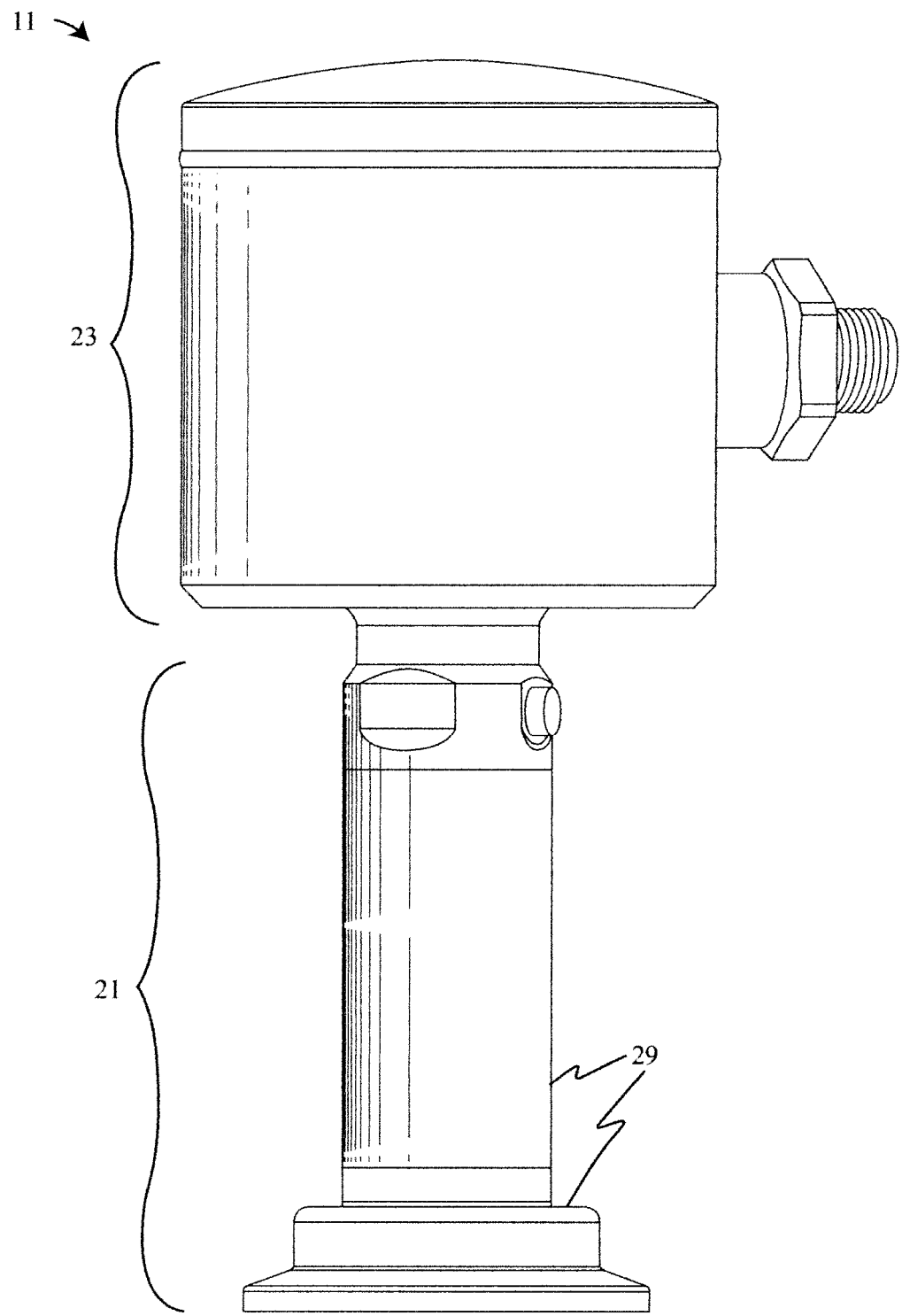
FIG. 1 is a front elevation of the sensor assembly of the present invention.

While one embodiment of the present invention is illustrated in the above referenced drawings and in the following description, it is understood that the embodiment shown is merely one example of a single preferred embodiment offered for the purpose of illustration only and that various changes in construction may be resorted to in the course of manufacture in order that the present invention may be utilized to the best advantage according to circumstances which may arise, without in any way departing from the spirit and intention of the present invention, which is to be limited only in accordance with the claims contained herein.

DETAILED DESCRIPTION OF AT LEAST ONE PREFERRED EMBODIMENT OF THE INVENTION

In the following description, numerous specific details are set forth such as examples of some preferred embodiments, specific components, devices, methods, in order to provide a thorough understanding of embodiments of the present disclosure. It will be apparent to a person of ordinary skill in the art that these specific details need not be employed, and should not be construed to limit the scope of the disclosure. In the development of any actual implementation, numerous implementation-specific decisions must be made to achieve the developer's specific goals, such as compliance with system-related and business-related constraints. Such a development effort might be complex and time consuming, but is nevertheless a routine undertaking of design, fabrication, and manufacture for those of ordinary skill.

A least one preferred embodiment of the present invention is illustrated in the drawings and figures contained within this specification. More specifically, certain preferred embodiments of the present invention are generally disclosed and described in FIGS. 1-6. It is appreciated by those of skill in the art that the following description contains only an exemplary embodiments of the present invention.

Referring now to the drawings, a sensor assembly 11 of the present invention is shown in FIG. 1. A partially exploded view is shown if FIG. 1A. Assembly 11 is designed for use in the automated process control for a hygienic material processing system 13 as illustrated in FIG. 2. In FIG. 2, assembly 11 is shown mounted in a position to sense the value of a process parameter (such as pressure of a fluid F) flowing in a pipe P. Assembly 11 communicates the value of the parameter via any standard communication protocol to a process controller 15 having a number of inputs and outputs 17 to control the process in a conventional manner. The present invention is not limited to any particular process control system, and is instead directed to assembly 11 for use in any such system. The process parameter is described herein as being the pressure of the liquid or other flowable material being processed, but could also be the level and/or the flow rate of the liquid and flowable material.

Turning back to FIGS. 1 and 1A, sensor assembly 11 includes a replaceable sensor module 21 and an assembly housing 23. Assembly housing 23 contains (see FIG. 3) an assembly housing processor (micro-controller) 25 and a loop transmitter and power supply circuit 27 connected to the assembly housing processor 25 and accessible by automated process control system 13. Two wire transmitter systems are well-known in process control systems. The transmitter and power supply 27 is connected to the loop (indicated by LOOP+ and LOOP− in the lower right-hand corner of FIG. 3) and is powered by the loop current flowing through the current loop. In fact, all the electronics of sensor assembly 11 are ultimately powered by the current from the current loop. The magnitude of the loop current is varied by loop transmitter and power supply 27 as a function of the magnitude of the process parameter variable being measured. Thus, the loop current is held at essentially a constant current value corresponding to the value of the parameter being measured, while at the same time all the needs of the circuitry in sensor assembly 11 are being supplied from the same current. This latter load is, of course variable, so the present invention requires monitoring of the loop current to ensure that it stays at the constant current value representing the measured parameter value despite the changing amount of current needed by the electronics in sensor assembly 11.

Figure 3:
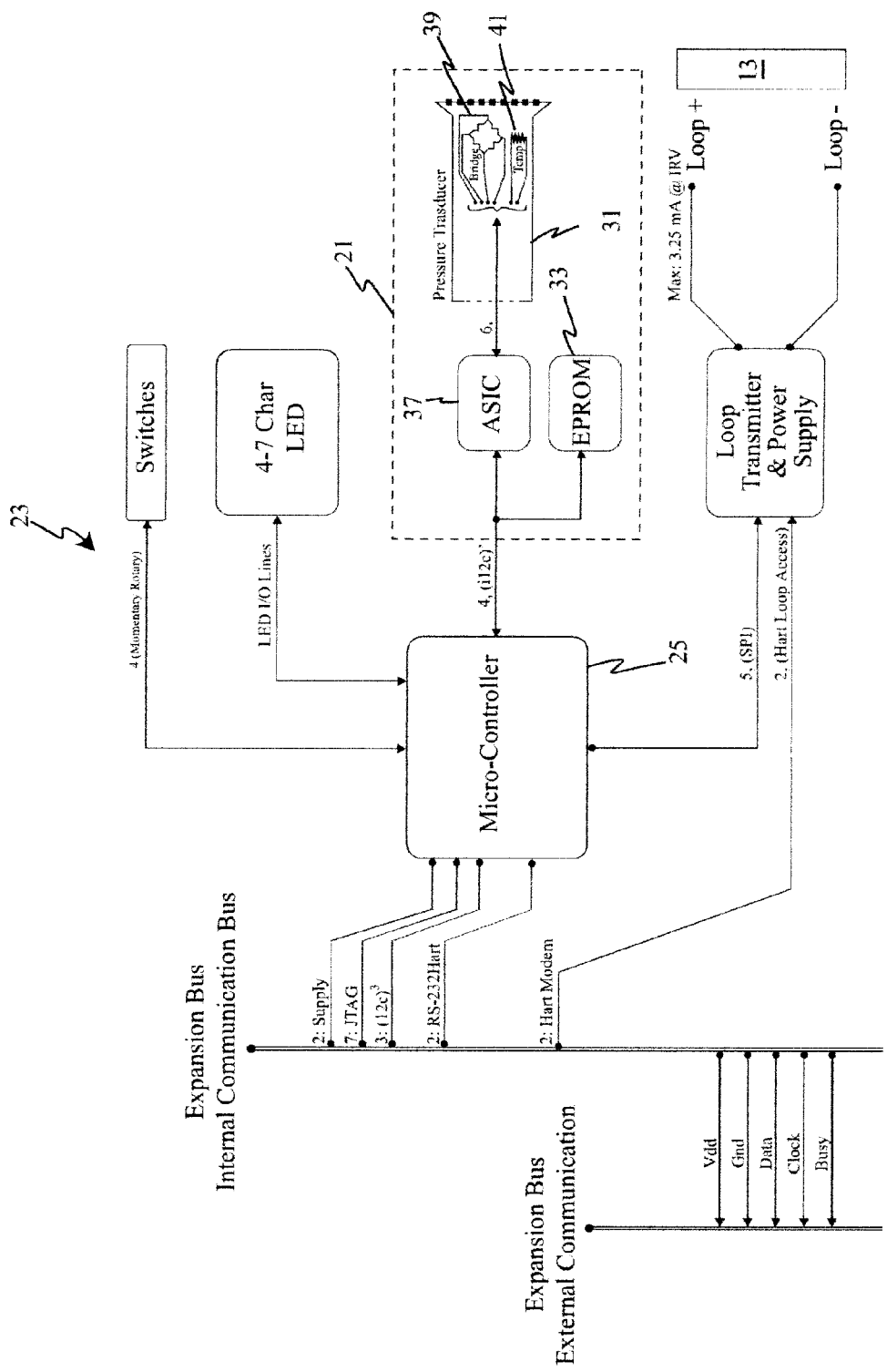
FIG. 3 is a block-diagram illustrating various electronic components contained in the sensor assembly of FIG. 1.
Figure 3A:
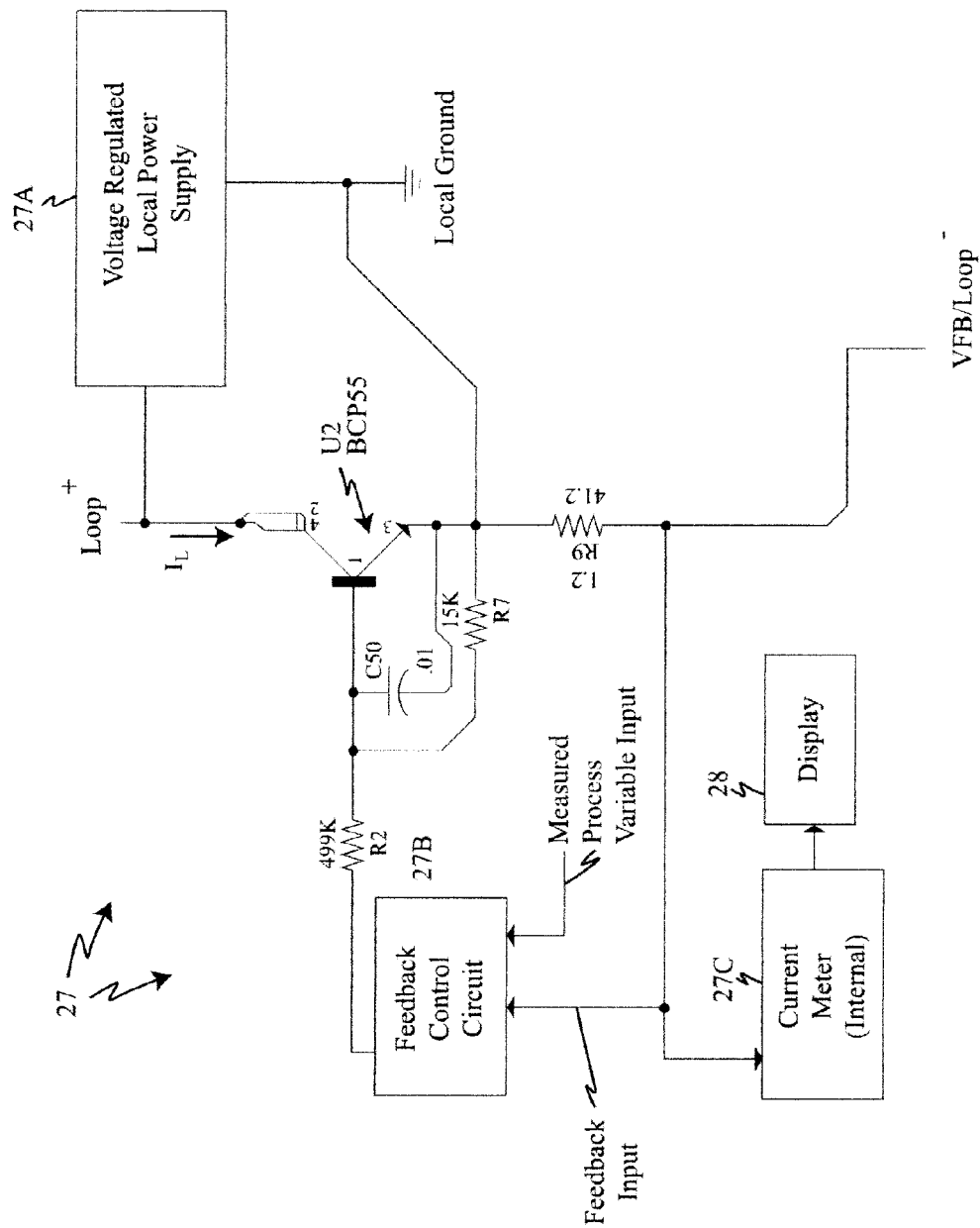
FIG. 3A is a schematic illustrating the transmitting/current measuring portion of the present invention.

Turning to FIG. 3A, loop transmitter and power supply 27 is shown in more detail, as including a power supply portion 27A and a negative feedback control circuit portion 27B. Power supply portion 27A supplies regulated power at a desired level to the rest of the circuitry of sensor assembly 11. For example, to supply regulated power at 3.3V, power supply portion 27A may include an output voltage regulator such as the type sold under the trade designation LTC3632 and a linear regulator such as the type sold under the trade designation TPS77033. Of course, any number of different such components could be used, and the particular type of components making up power supply portion 27A is not considered to be part of the present invention.

The loop current IL flows between the terminals of the loop, labeled Loop+ and Loop− as indicated in FIG. 3A. The magnitude of that current is governed by NPN transistor U2, which may preferably be that sold under the trade designation BCP55. The collector of transistor U2 is connected to current loop terminal Loop+, while the emitter is connected through a feedback resistor R9 to the other loop terminal Loop−. The voltage drop across resistor R9 is supplied to a conventional feedback control circuit which constitutes the transmitter portion 27A of the circuitry. This feedback control circuit uses the voltage drop across resistor R9, which is a direct measure of the current flowing in the loop and an input representing the value of measured process variable, and supplies a corresponding signal to the base of transistor U2 (FIG. 3A) The feedback control circuit is conventional in construction. For example, it can preferably be configured using an amplifier sold under the trade designation OPA4379. The precise details of such feedback circuits and their use in transmitting data over two-wire current loops are well-known and are not considered to be part of the present invention.

The feedback signal is preferably also supplied to an internal current meter 27C of the present invention. More specifically, the feedback signal is measured using an analog-to-digital converter (ADC). Such an ADC may be present in many available ASIC chips. For example, the ASIC chip sold under the trade designation ZMD31050 has a built-in ADC which is suitable for this task. The ASIC (or alternatively, micro-controller 25) uses this converted digital value to compute the actual loop current. More specifically, the processor in the ASIC or the micro-controller itself uses an equation to compute the actual current value corresponding to the measured value of the feedback signal. A first order linear equation has been found to adequate for this task, although higher order equations could also be used. The current loop value, after it is calculated is then displayed on a suitable display such as display 28. The 4×7-CHAR LED display shown in FIG. 3 may be used for display 28, or other suitable display may be provided.

Figure 4:
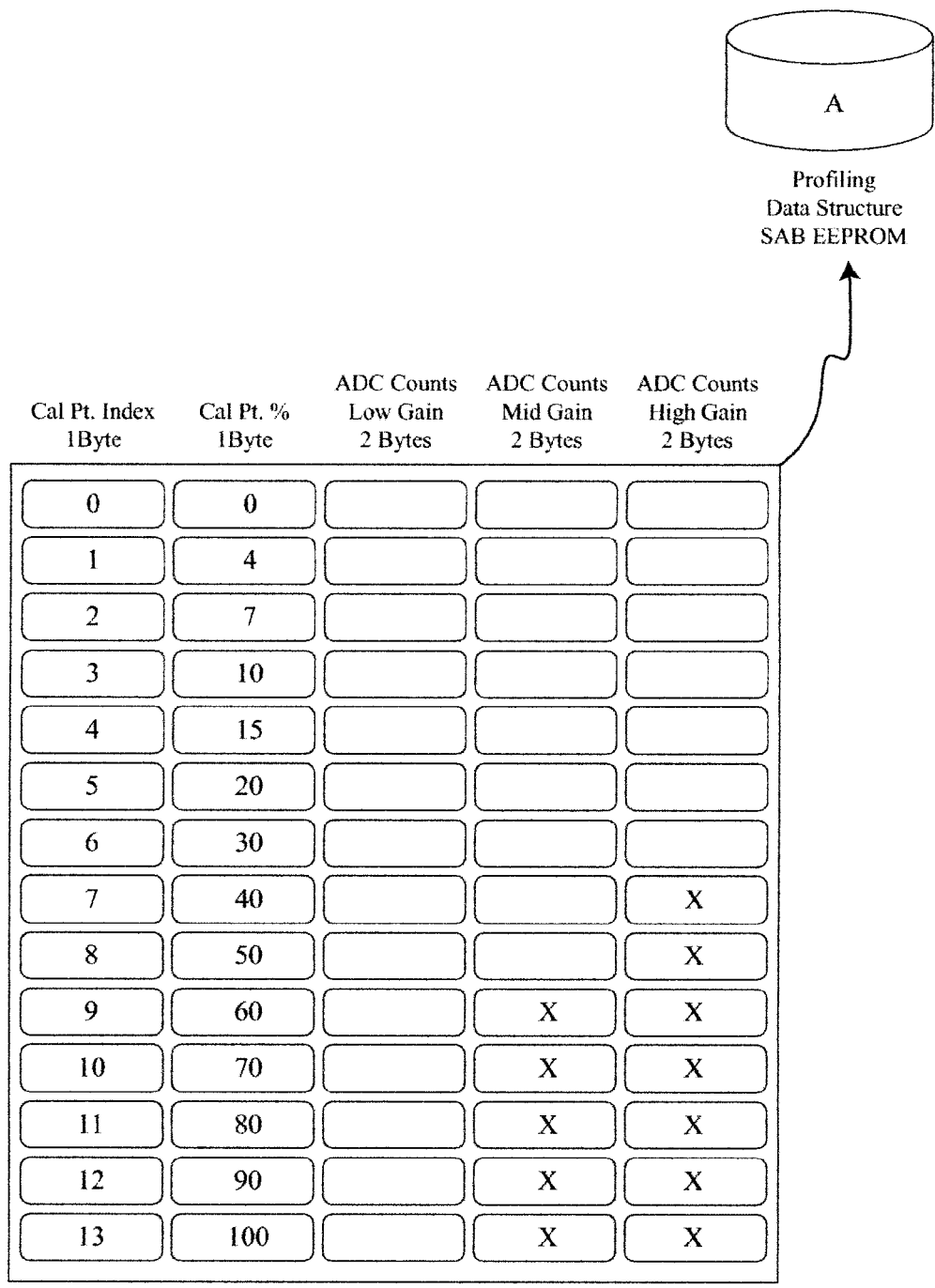
FIG. 4 illustrates the data structure of profiling data stored in the sensor assembly, and more particularly in the sensor module portion of the sensor assembly.

Turning back to FIG. 1, replaceable sensor module 21 includes an enclosure or housing 29 (FIG. 1) adapted to be mounted in a position to sense the process variable. A process variable transducer 31 is positioned in enclosure 29 so as to be exposed to the process variable. A non-volatile memory 33 (shown as an EEPROM) is also disposed in sensor module 21 and has stored therein specific profiling data for the sensor module. More specifically (see FIG. 4), EEPROM 33 has stored therein the pressure-temperature characteristics for that particular sensor module 21. That is, the contents of EEPROM 33 vary from sensor module to sensor module as a function of the particular transducer 31 contained in the sensor module. As shown in FIG. 4, the profiling data preferably includes data taken at three different gain levels (Low, Mid, and High) at multiple different points across its range.

Turning back to FIG. 3, it is preferred that sensor module 21 include its own processor 37 (which in FIG. 3 is an ASIC chip) which is connected to pressure transducer 31 and to EEPROM 33. ASIC 37 includes and analog-to-digital converter (ADC) to convert the output of the process parameter transducer 31 to digital values. It is these ADC values which constitute the recorded profiling data indicated in FIG. 4. As a result, it should be noted that the profiling data stored is a function not only of the particular transducer in the sensor module, but also of the particular ASIC chip.

As shown in FIG. 3, transducer 31 (not shown) using a bridge 39 to sense the process parameter (in this example, pressure). That transducer includes a strain gage mounted on a diaphragm, which is described below. In addition, a temperature transducer 41 is included in transducer 31 for supplying temperature information to ASIC 37. It should be understood that the present invention is not limited to the use of any particular type of sensor for sensing the desired process parameter. Although at present ASIC 37 is contemplated as being a CMOS integrated circuit chip sold under the trade designation ZMD31050, it should also be understood that any ASIC capable of performing these functions could be used. This particular chip is useful since it has the ability to test the lumped resistance of the bridge 39 under programmed control. This chip is designed to electrically short across the bridge (which effectively cancels the load on the sensor) and measure the lumped resistance (common mode voltage) of the bridge. ASIC 37 is programmed to measure this electrical characteristic of the transducer periodically between actual process readings. In addition, high (upper) and low (lower) thresholds are set in ASIC 37 so that measurements outside the thresholds are identified. This state can be indicated either electrically, visually, or both. This feature allows drift of the sensor due to age, adverse conditions, etc. to be detected so that the system can be recalibrated.

Note that EEPROM 33 is connected to both ASIC 37 and the housing processor 25. Specifically, sensor module 21 is connected to micro-controller 25 by an i2c communication bus (although the particular communications protocol is not a feature of this invention). The profiling information from the EEPROM is supplied to ASIC 37 so that the digital output of ASIC 37 to housing processor 25 preferably provides fully calibrated digital sensor readings. The information is also supplied to the housing processor. Housing processor 25 is responsive to this information to generate a calibration curve (by way of example, a third order calibration curve) which it supplies to ASIC 37. Housing processor 25 is also responsive to this information and to its own data representing the desired sensor assembly output characteristics for that particular sensor assembly to provide the desired sensor assembly output characteristic when connected to the sensor module having the specified profiling data. In this way, sensor module 21 can be used with any number of different assembly housing 23 to provide the correct output for that particular sensor assembly at that particular location. This significantly reduces the necessary inventory of sensor modules.

Turning back to FIG. 1A it can be seen that sensor module 21 includes a screw thread 41a by which the sensor module 21 is secured to a mating surface in assembly housing 23 to secure the sensor module and the assembly housing into a single unitary structure. It is preferred that the sensor module and the assembly housing be capable of being secured together by hand, without the use of hand tools. Alternatively, the sensor module 21 may be secured to assembly housing 23 by corresponding bayonet-connector type structures, which are well known in the art. In the later case, mechanical connection of the sensor module to the assembly housing automatically provides the required electrical connection therebetween. Bayonet-type electrical connectors are well known. Other connectors such as push-pull electrical connectors such as those sold by LEMO S.A. may also be used to provide simultaneous electrical and mechanical connection.

Figure 1A:
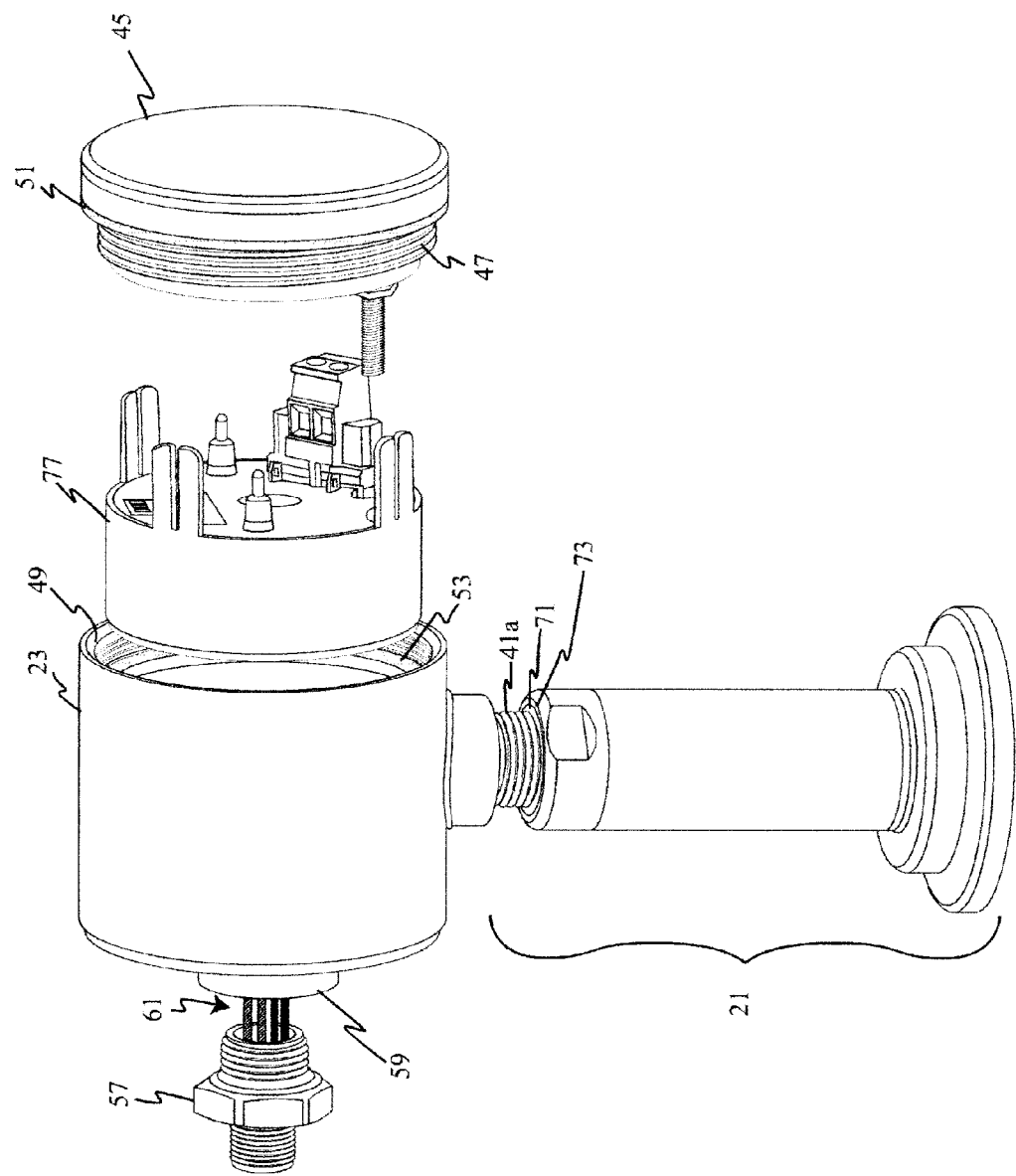
FIG. 1A is an exploded view of the sensor assembly of FIG. 1.

As shown in FIG. 1A, sensor assembly 11 includes a transparent cover 45 with screw threads 47 which together with mating threads 49 on the interior of assembly housing 23 permit the cover to be attached to the assembly housing. The attachment of cover 45 to assembly housing 23 potential creates a path for migration of moisture from the exterior of the assembly housing to the interior of assembly housing 23. For this reason, an o-ring 51 is disposed on cover 45 and a second o-ring 53 is disposed in assembly housing 23. (In FIG. 1B, various parts have been removed to more clearly show the o-rings.) When cover 45 is properly screwed onto assembly housing 23, both o-ring 51 and o-ring 53 provide moisture-resistant seals between the cover and the assembly housing. Note as well that attaching cover 45 to assembly housing 23 causes o-ring 51 to be axially compressed, while that same action causes o-ring 53 to be radially compressed. Each of these seals, therefore, provides an independent seal, with different modes of failure, thereby maximizing the possibility of preventing moisture from entering the interior of assembly housing 23. O-ring 51 is positioned such that when the cover is properly sealed to assembly housing 23 that fact can be visually verified. It is also preferred that both o-rings provide a suitable tactile sensation when cover 45 is properly sealed to assembly housing 23.

Figure 1B:
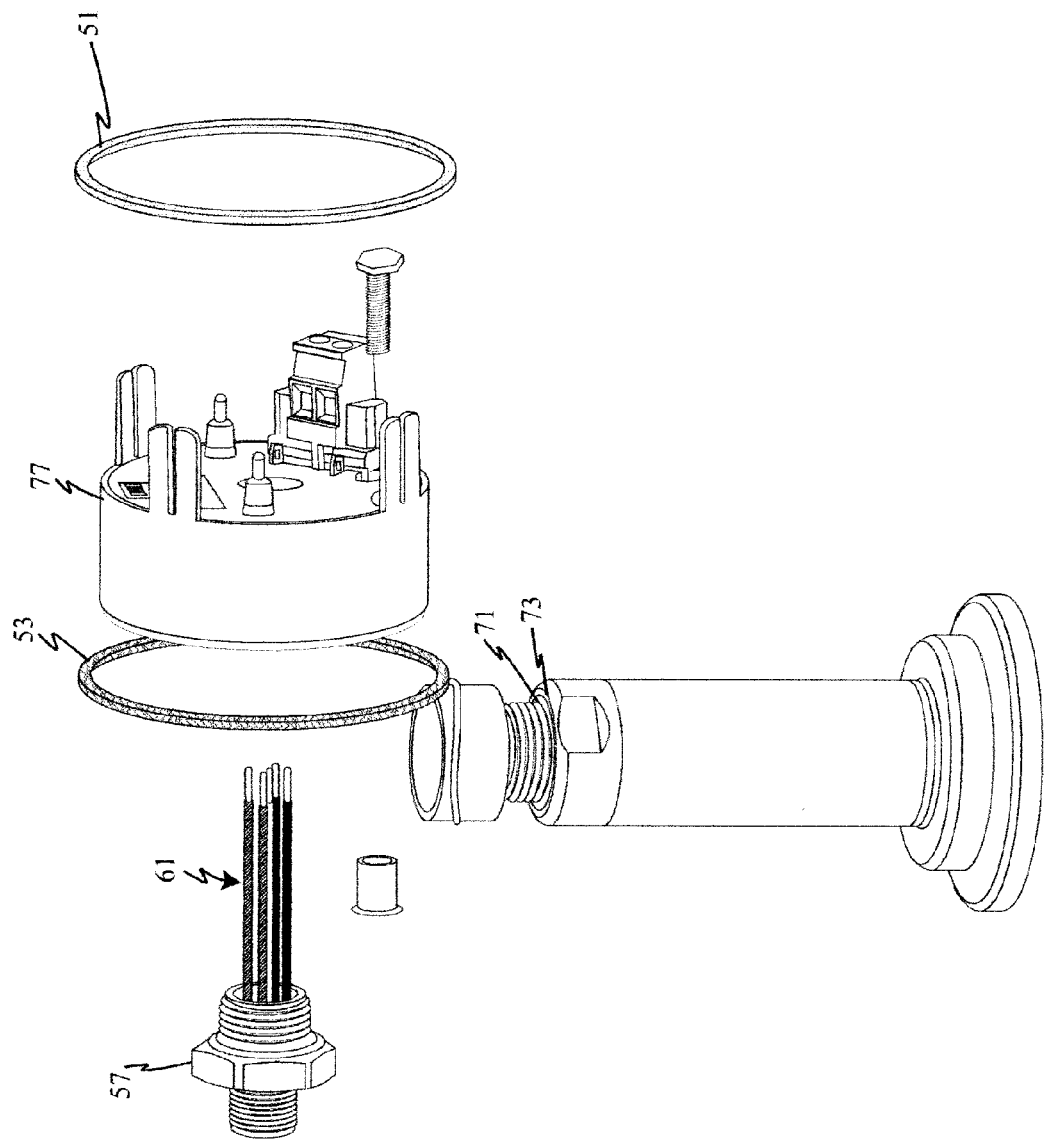
FIG. 1B is an exploded view like FIG. 1A with parts broken away for clarity.
Figure 2:
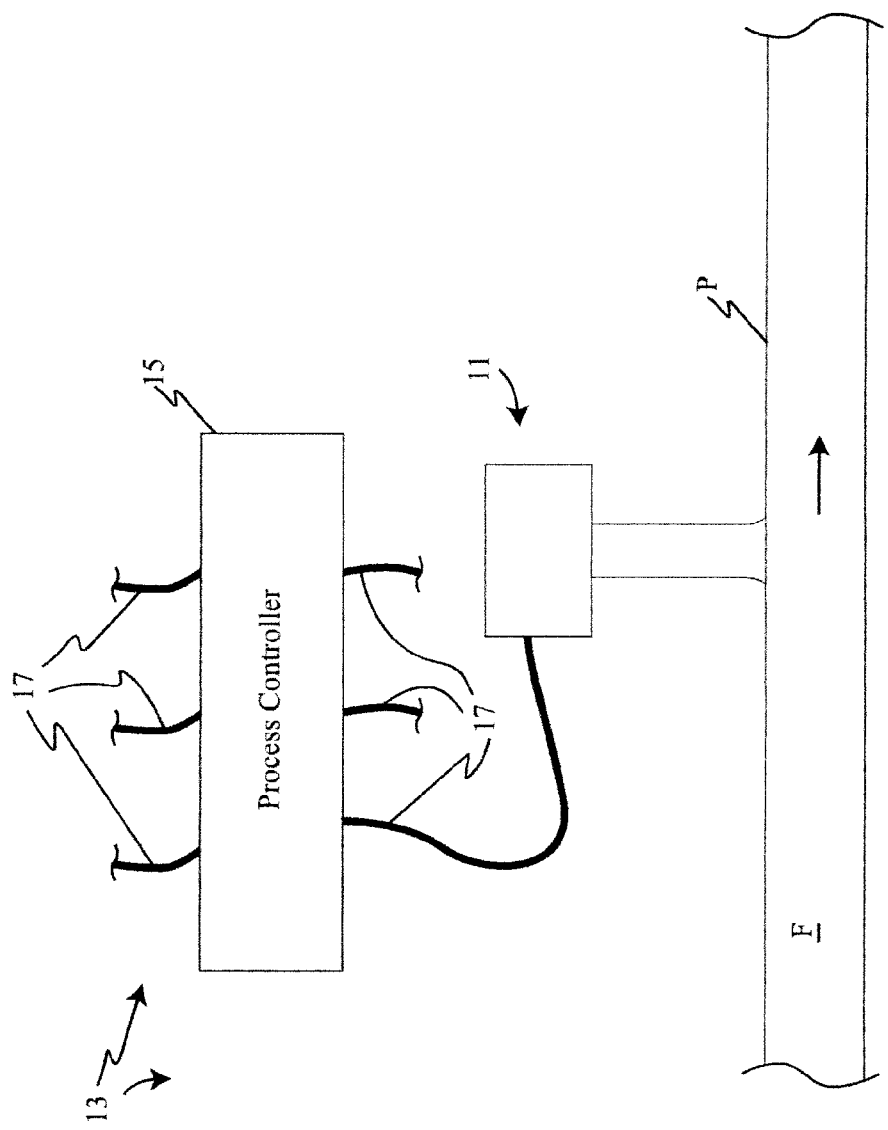
FIG. 2 is a diagrammatic view illustrating the use of the sensor assembly of the present invention.
Figure 5:
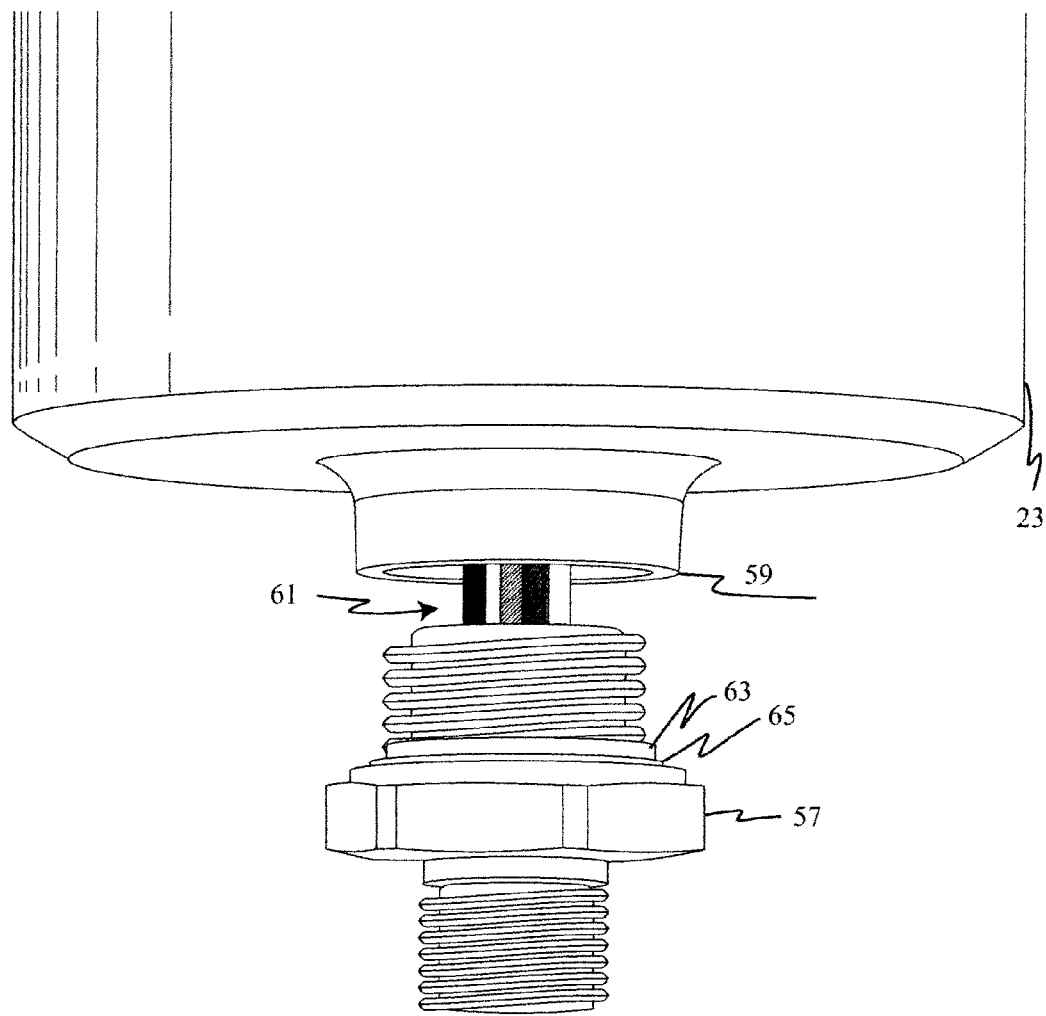
FIG. 5 is an exploded view with parts broken away of the mechanical connection of one portion of the sensor assembly to the main housing of the assembly.
Figure 5A:
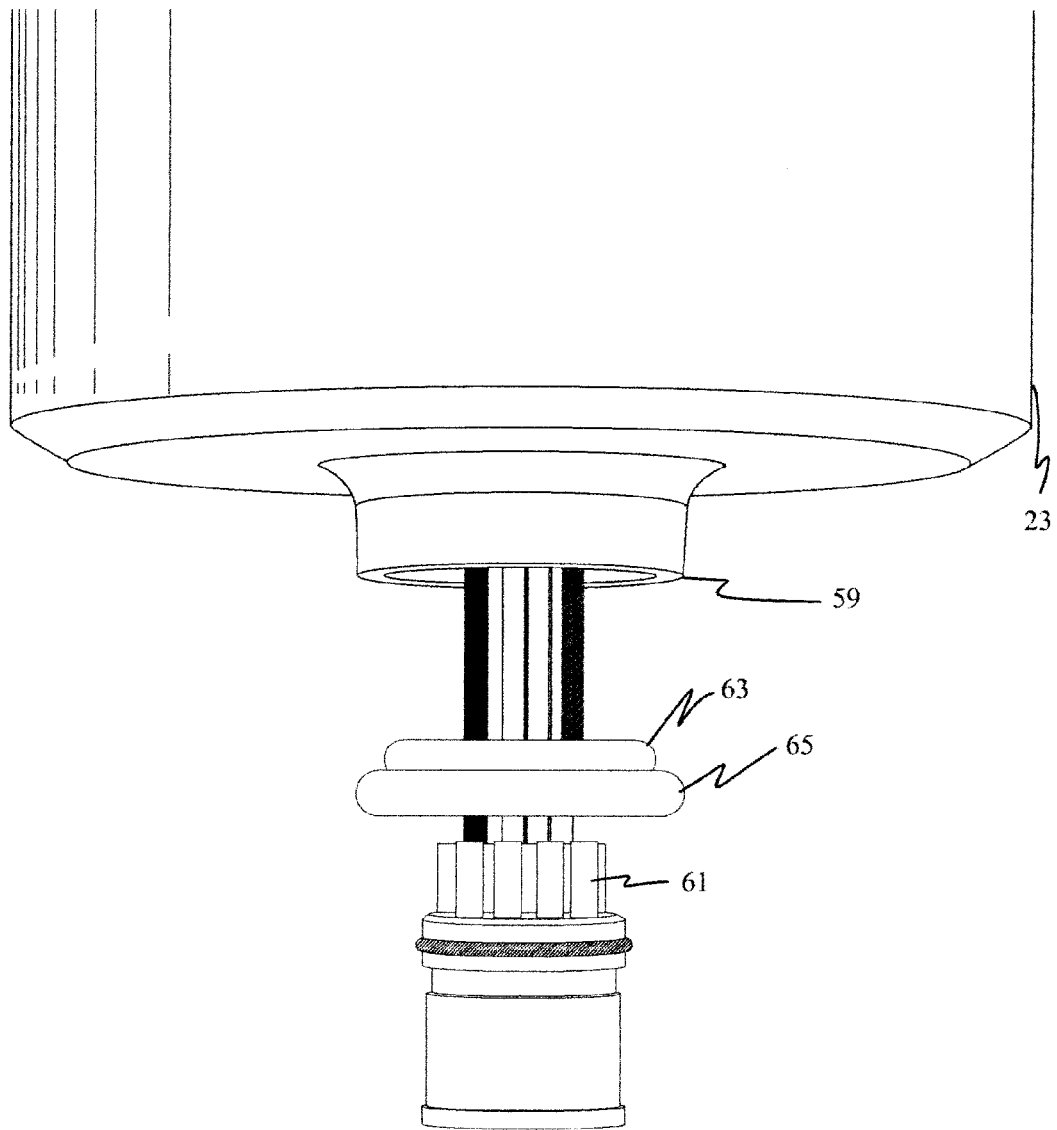
FIG. 5A is an exploded view like FIG. 5 with additional parts broken away for clarity, illustrating an axial and radial sealing feature of the present invention.
Figure 6:
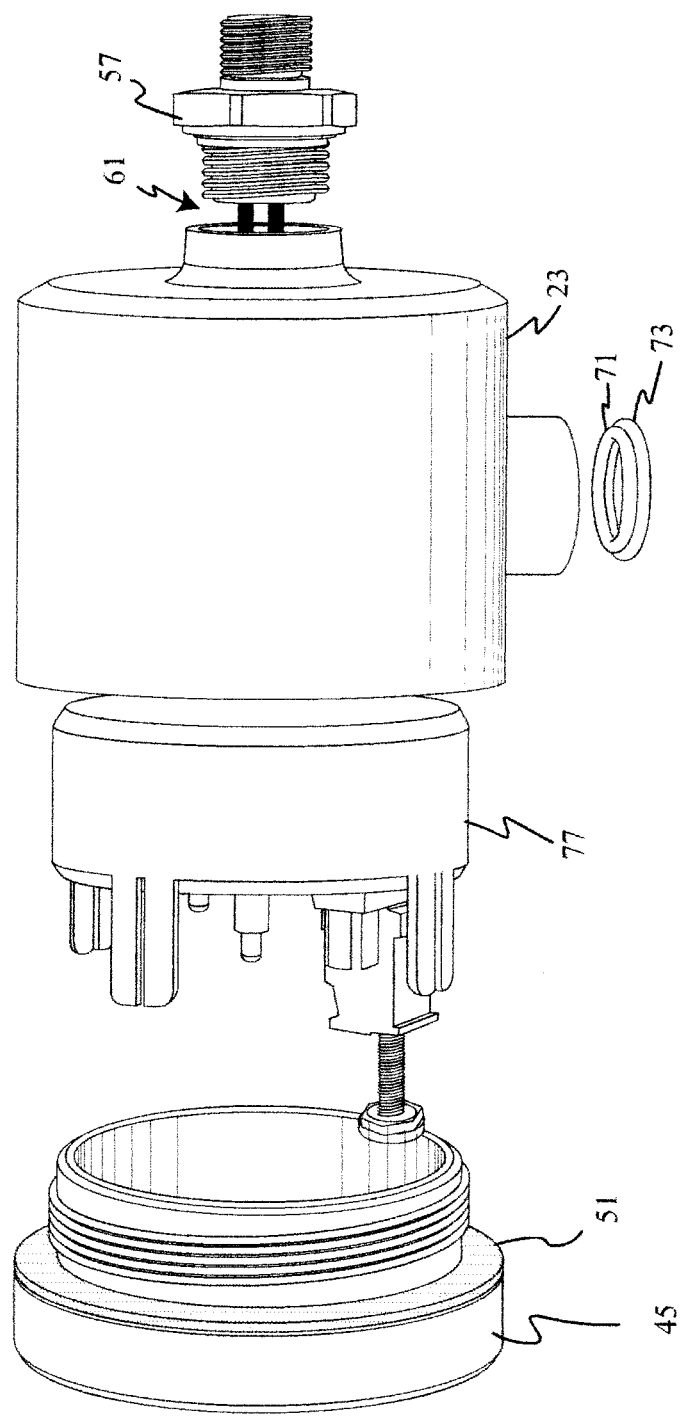
FIG. 6 is an exploded view of the sensor assembly with parts broken away to illustrate additional axial and radial sealing features of the present invention.

Also shown in FIGS. 1A and 1B are a threaded plug 57 for attachment to a corresponding threaded sleeve 59 (FIG. 1A only) of assembly housing 23. The electrical connector 61 for making connection between the micro-controller 25 and the process controller 15 extends through plug 57. Threaded sleeve 59 potentially creates a second path for migration of moisture into the assembly. As can be seen in FIGS. 5 and 5A, a pair of o-rings 63 and 65 are disposed between plug 57 and mating sleeve 59 to provide axial and radial seals to prevent such a migration of moisture into the assembly.

The connection between sensor module 21 and assembly housing 23 also provides a potential path for moisture migration into the assembly housing. A pair of o-rings 71, 73 (FIGS. 1A, 1B, and 6) are disposed in such a manner as to provide axial and radial seals such as described above in connection with the other two migration paths.

Also shown in FIGS. 1A and 1B is a block 77 which includes the various electronic components contained within assembly housing 23. Securing cover 45, plug 57, and sensor module 21 to the assembly housing 23 as described above provides a redundant, moisture resistant seal for the entire assembly housing. Note that many of the seals are coaxial. However, the seals formed by o-rings 71 and 73, while coaxial to each other, are positioned transversely relative to the position of the seals formed by the other o-rings. The seals formed by sensor module o-rings 61 form seals which are adjacent each other. This is also true of o-rings 71 and 73. The o-rings 51 and 53 which form the seals for cover 45 are more widely spaced apart, but they still provide both axial and radial sealing.

In the preceding description, numerous specific details are set forth such as examples of specific components, devices, methods, in order to provide a thorough understanding of embodiments of the present disclosure. It will be apparent to a person of ordinary skill in the art that these specific details need not be employed, and should not be construed to limit the scope of the disclosure. In the development of any actual implementation, numerous implementation-specific decisions must be made to achieve the developer's specific goals, such as compliance with system-related and business-related constraints. Such a development effort might be complex and time consuming, but is nevertheless a routine undertaking of design, fabrication and manufacture for those of ordinary skill. The scope of the invention should be determined by any appended claims and their legal equivalents, rather than by the examples given.

Additionally, it will be seen in the above disclosure that several of the intended purposes of the invention are achieved, and other advantageous and useful results are attained. As various changes could be made in the above constructions without departing from the scope of the invention, it is intended that all matter contained in the above descriptions or shown in the accompanying drawings shall be interpreted as illustrative and not in a limiting sense.

Terms such as "proximate," "distal," "upper," "lower," "inner," "outer," "inwardly," "outwardly," "exterior," "interior," and the like when used herein refer to positions of the respective elements as they are shown in the accompanying drawings, and the disclosure is not necessarily limited to such positions. Terms such as "first," "second," and other numerical terms when used herein do not imply a sequence or order unless clearly indicated by the context.

When introducing elements or features and the exemplary embodiments, the articles "a," "an," "the" and "said" are intended to mean that there are one or more of such elements or features. The terms "comprising," "including," and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It will also be understood that when an element is referred to as being "operatively connected," "connected," "coupled," "engaged," or "engageable" to and/or with another element, it can be directly connected, coupled, engaged, engageable to and/or with the other element or intervening elements may be present. In contrast, when an element is referred to as being "directly connected," "directly coupled," "directly engaged," or "directly engageable" to another element, there are no intervening elements present. Other words used to describe the relationship between elements should be interpreted in a like fashion (e.g., "between" versus "directly between," "adjacent" versus "directly adjacent," etc.).

What is claimed is:

1. A sensor assembly having a replaceable sensor module, with the sensor assembly being adapted to be positioned in a flow stream of material flowing in a hygienic material processing system for sensing parameters of the material and generating signals for use by an automated process controller for controlling the operation of the hygienic material processing system, the sensor assembly comprising:

a first module constituting a replaceable sensor module;

a second module constituting a data processing module, with the first and second modules being detachably secured to each other via a mechanical interconnection and being in electrical communication with each other via an electrical interconnection, wherein the replaceable sensor module comprises:

a generally cylindrical enclosure adapted to be mounted in a position in a flow stream of a material;

a transducer positioned in the enclosure toward a first end of the second sensor module for sensing parameters of the material;

at least one electronic circuit connected to said transducer for generating sensor data indicative of parameters of the material; and, a non-volatile memory having stored therein identification data for the transducer;

wherein the data processing module comprises:

a housing having a microprocessor adapted to receive sensor data and identification data from the replaceable sensor module, wherein the microprocessor has a memory that stores transducer calibration information relating to a range of identified transducers for enabling different sensor modules, each with potentially unique calibration characteristics to be used with the data processing module, and wherein the data processing module generates signals as a function of the sensor data and the identification data for use by an automated process controller for controlling the operation of the hygienic material processing system, and wherein the mechanical interconnection comprises a first O-ring and a second O-ring of generally annular configuration for blocking leakage of material in the flow stream past the mechanical interconnection from entering the data processing module, wherein the first O-ring and the second O-ring are positioned at a second end of the sensor module enclosure generally coaxially therewith, wherein the first O-ring seal is subjected to compression in an axial direction of the sensor module enclosure when the sensor module is secured to the data processing module, and wherein the second O-ring seal is subjected to compression in a radial direction of the sensor module enclosure when the sensor module is secured to the data processing module.

2. The sensor assembly as set forth in claim 1 wherein mechanical interconnection further comprises a first mating surface on the replaceable sensor module and a second and corresponding mating surface on the data processing module adapted to mate with the first mating surface of for detachably securing the replaceable sensor module to the data processing module to form a unitary sensor assembly structure.

3. The sensor assembly as set forth in claim 2 wherein the mating surfaces are threaded.

4. The sensor assembly as set forth in claim 2 wherein the electrical connection provides electrical communication between the first and second modules when the mechanical interconnection secures the first and second modules together.

5. The sensor assembly as set forth in claim 2 wherein the electrical interconnection comprises an electrical connector at the second end of the sensor module and an electrical connector on the data processing module that are engaged when the first and second modules are assembled together.

6. The sensor assembly as set forth in claim 2 wherein the mechanical interconnection is adapted to be manually engaged to make and break the mechanical connection between the first and second modules without the need of tools.

7. The sensor assembly as set forth in claim 6 wherein the mechanical interconnection provides a visual indication to notify a user if one of either the first O-ring or the second O-ring are not properly seated after the first module has been assembled to the second module.

8. The sensor assembly as set forth in claim 6 wherein the mechanical interconnection provides a tactile indication to notify a user if one of either the first O-ring or the second O-ring are not properly seated after the first module has been assembled to the second module.

9. The sensor assembly as set forth in claim 1 wherein the parameter of the material is selected from the group consisting of a parameter indicative of pressure of the material, a parameter indicative of temperature of the material, a parameter indicative of volume of the material, and a parameter indicative of flow rate of the material.

10. The sensor assembly as set forth in claim 1 wherein the identification data for the transducer stored in the non-volatile memory includes pressure-temperature characteristics for the transducer in the replaceable sensor module.

11. The sensor assembly as set forth in claim 1 wherein the microprocessor in the data processing module uses calibration information to generate a calibration curve for the sensor assembly.

12. The sensor assembly as set forth in claim 1 wherein the replaceable sensor module includes a temperature in addition to the process variable transducer.

13. The sensor assembly as set forth in claim 1 further comprising a cover formed at least in part of a transparent material and detachably secured to the data processing module, with the cover closing a corresponding opening in the data processing module when secured to the data processing module.

14. The sensor assembly as set forth in claim 13 further comprising a third O-ring and a fourth O-ring of generally annular configuration positioned adjacent the cover and generally coaxially therewith, with the third O-ring being subjected to compression in a axial direction of the cover and the fourth O-ring being subjected to compression in the radial direction of the cover when the cover is detachably secured to the data processing module.

* * * * *